US009107587B2

(12) United States Patent
Chemla et al.

(10) Patent No.: US 9,107,587 B2
(45) Date of Patent: Aug. 18, 2015

(54) DEVICE AND PROCESS FOR CALCULATING NEW INDICES OF ARTERIAL STIFFNESS, AND/OR FOR STROKE VOLUME MONITORING

(75) Inventors: Denis Chemla, Paris (FR); Karsten Plamann, Palaiseau (FR); Alain Nitenberg, Villeneuve la Garenne (FR)

(73) Assignees: Universite Paris SUD, Orsay Cedex (FR); Assistance Publique-Hopitaux de Paris, Paris Cedex (FR); Universite Paris 13, Villetaneuse (FR); Ecole Normale Superieure de Technoiques Avancees, Paris Cedex (FR)

( * ) Notice: Subject to any disclaimer, the term of this patent is extended or adjusted under 35 U.S.C. 154(b) by 739 days.

(21) Appl. No.: 12/866,317

(22) PCT Filed: Feb. 12, 2009

(86) PCT No.: PCT/EP2009/051647
§ 371 (c)(1),
(2), (4) Date: Aug. 5, 2010

(87) PCT Pub. No.: WO2009/101140
PCT Pub. Date: Aug. 20, 2009

(65) Prior Publication Data
US 2010/0317976 A1  Dec. 16, 2010

Related U.S. Application Data

(60) Provisional application No. 61/029,013, filed on Feb. 15, 2008.

(51) Int. Cl.
*A61B 5/02* (2006.01)
*A61B 5/0215* (2006.01)
*A61B 5/021* (2006.01)
(Continued)

(52) U.S. Cl.
CPC ............... *A61B 5/0215* (2013.01); *A61B 5/02* (2013.01); *A61B 5/021* (2013.01); *A61B 5/02007* (2013.01); *A61B 5/029* (2013.01); *A61B 5/1455* (2013.01)

(58) Field of Classification Search
USPC .......................................................... 600/485
See application file for complete search history.

(56) References Cited

U.S. PATENT DOCUMENTS 5,183,051 A     2/1993  Kraidin et al.
2006/0173248 A1*  8/2006  Karamanoglu et al. ...... 600/301
(Continued)

FOREIGN PATENT DOCUMENTS

EP    1584289 A2   10/2005

OTHER PUBLICATIONS

Mitchell, Gary F. Pheiffer, Mark A. May 2005. American Heart Journal, vol. 149, Issue 5, pp. 776-784.*
(Continued)

*Primary Examiner* — Michael Kahelin
*Assistant Examiner* — Mitchell E Alter
(74) *Attorney, Agent, or Firm* — Greer, Burns & Crain, Ltd.

(57) ABSTRACT

A process for calculating an indice of arterial stiffness, including the step of extracting pulse wave analysis data from a recorded pressure of an artery, the recorded pressure is recorded as a function of time, the indice being calculated as a function of the extracted data, and the extracted pulse wave analysis data including at least one time interval.

37 Claims, 5 Drawing Sheets

(51) Int. Cl.
*A61B 5/029* (2006.01)
*A61B 5/1455* (2006.01)

(56) References Cited

U.S. PATENT DOCUMENTS

2007/0191724 A1 8/2007 Hirsh
2007/0197924 A1* 8/2007 O'Rourke .................... 600/504
2007/0293771 A1* 12/2007 Noren et al. ................. 600/481

OTHER PUBLICATIONS

Liu, Z. et al., Estimation of Total Arterial Compliance: An Improved Method and Evaluation of Current Methods.*
Lamia, B., et al., Contribution of Arterial Stiffness and Stroke Volume to Peripheral Pulse Pressure in ICU Patient: An Arterial Tonometry Study.*
Sherrid, M. et al. "Reflections of Inflections in Hypertrophic Cardiomyopathy" Journal of the American College of Cardiology, vol. 54, No. 3, 2009.*

* cited by examiner

DEVICE AND PROCESS FOR CALCULATING NEW INDICES OF ARTERIAL STIFFNESS, AND/OR FOR STROKE VOLUME MONITORING

PRIORITY CLAIM

Applicant claims priority benefits under 35 U.S.C. §119 on the basis of Patent Application No. 61/029,013, filed Feb. 15, 2008.

BACKGROUND

The present invention relates to a process for calculating a new indice of arterial stiffness and/or a stroke volume, and to a device implementing this process.

Typically, a process or device according to the invention can be used for monitoring the stroke volume. In this case, the process or device according to the invention can be used in a medical or surgical Intensive Care Unit (ICU) and in an anesthesia unit, wherein such monitoring can be very useful.

Key Words: arterial stiffness, pulse pressure, hypertension, left ventricle, afterload, heart rate, cardiovascular risk factors, stroke volume A growing number of clinical and epidemiological studies use aortic pulse contour analysis to document the role of increased pulsatile load and arterial stiffness throughout aging in subjects exposed to cardiovascular risk factors and in patients with various cardiovascular diseases [1-6]. Aortic pulse wave may be obtained from invasive catheterization or estimated from noninvasive techniques (eg, applanation tonometry).

Total arterial stiffness plays a contributory role throughout aging and in numerous cardiovascular diseases, including hypertension. Aortic stiffening is responsible for an increased characteristic impedance (ie, the impedance to the left ventricular pulsatile flow), thus increasing the forward pressure-wave amplitude that contributes to pulse pressure elevation. Aortic stiffening also increases pulse wave velocity, and this results in anticipated and enhanced wave reflections, further augmenting central pulse pressure. Unfortunately, there is no simple estimate of characteristic impedance. Furthermore, recent guidelines have reviewed the limitations of diastolic pulse contour analysis to estimate arterial stiffness.

The goal of the invention is to present a process and device for providing new and simple indices quantifying pulsatile load and/or arterial stiffness in humans, and/or for providing new and simple calculation of a stroke volume.

SUMMARY

An aspect of the invention concerns a process for calculating an indice of arterial stiffness, comprising the step of extracting pulse wave analysis data from a recorded pressure of an artery, the process being characterized in that the recorded pressure is recorded as a function of time, the indice being calculated as a function of the extracted data, the extracted pulse wave analysis data comprising at least one time interval. Thus, the indice of arterial stiffness is calculated as a function of the at least one time interval.

The extracted pulse wave analysis data can comprise at least one pressure. Thus, in this case, the indice of arterial stiffness is calculated as a function of the at least one pressure.

The at least one time interval can comprise a systolic time, the indice being calculated as a function of the systolic time.

The at least one time interval can comprise a time to the pressure at an inflection point during systole, the indice being preferably calculated as a function of the ratio:

$$ST/\Delta t,$$

where $\Delta t$ is the time to the pressure at the inflection point during systole and ST is the systolic time.

The at least one time interval can comprise a period of the artery, the indice being preferably calculated as a function of the ratio:

$$ST/T,$$

where T is the period and ST is the systolic time.

The indice can be calculated as a function of a recorded stroke volume. The extracted pulse wave analysis data can comprise:
 a diastolic pressure,
 a pressure at an inflection point during systole,
the indice being preferably calculated as a function of the following ratio:

$$[Pi-DAP]/SV,$$

where DAP is the diastolic pressure, Pi is the pressure at the inflection point during systole, and SV is the recorded stroke volume.

The at least one time interval can comprise a systolic time and the indice is preferably calculated as a function of the following ratio:

$[(Pi-DAP)*ST]/SV$, where DAP is the diastolic pressure, Pi is the pressure at the inflection point during systole, SV is the recorded stroke volume, and ST is the systolic time. The at least one time interval can comprise a time to the pressure at the inflection point during systole, and the indice is preferably calculated as a function of the following ratio:

$$[(Pi-DAP)*ST]/(SV*\Delta t),$$

where DAP is the diastolic pressure, Pi is the pressure at the inflection point during systole, SV is the recorded stroke volume, ST is the systolic time, and $\Delta t$ is the time to the pressure at the inflection point during systole.

The indice of arterial stiffness can be a characteristic impedance. In this case, the extracted pulse wave analysis data can comprise:
 a diastolic pressure,
 a pressure at an inflection point during systole,
the at least one time interval can comprise a systolic time, the characteristic impedance being preferably calculated according to the following equation:

$$Zc=[(Pi-DAP)*ST]/(2SV),$$

where Zc is the characteristic impedance, DAP is the diastolic pressure, Pi is the pressure at the inflection point during systole, SV is a recorded stroke volume, and ST is the systolic time.

The indice of arterial stiffness can be a total arterial compliance. In this case, the extracted pulse wave analysis data can comprise:
 a diastolic pressure,
 a pressure at an inflection point during systole,
the at least one time interval can comprise a systolic time and a time to the pressure at the inflection point during systole, the total arterial compliance being preferably calculated according to the following equation:

$$C=(SV*\Delta t)/[(Pi-DAP)*ST],$$

where C is the total arterial compliance, DAP is the diastolic pressure, Pi is the pressure at the inflection point during systole, SV is a recorded stroke volume, ST is the systolic time, and Δt is the time to the pressure at the inflection point during systole.

The indice of arterial stiffness can be a total arterial stiffness. In this case, the extracted pulse wave analysis data can comprise:
- a diastolic pressure,
- a pressure at an inflection point during systole, the at least one time interval can comprise a systolic time and a time to the pressure at the inflection point during systole, the total arterial stiffness being preferably calculated according to the following equation:

$$1/C=[(Pi-DAP)*ST]/(SV*\Delta t),$$

where 1/C is the total arterial stiffness, DAP is the diastolic pressure, Pi is the pressure at the inflection point during systole, SV is a recorded stroke volume, ST is the systolic time, and Δt is the time to the pressure at the inflection point during systole.

The indice of arterial stiffness can be a waveguide function. In this case, the extracted pulse wave analysis data can comprise:
- a diastolic pressure,
- a pressure at an inflection point during systole,
- a mean aortic pressure,
- a mean downstream pressure, the at least one time interval can comprise a systolic time and a period of the artery, the waveguide function being preferably calculated according to the following equation:

$$Zc/Rs=[(Pi-DAP)/(MAP-Po)]*[(ST)(2T)],$$

where Zc/Rs is the waveguide function, DAP is the diastolic pressure, Pi is the pressure at the inflection point during systole, ST is the systolic time, T is the period, MAP is the mean aortic pressure and Po is the mean downstream pressure.

This process for calculating an indice of arterial stiffness according to the invention can comprise a calibration of the indice, this calibration being preferably set with the previous calculation of the indice, and the process can further comprise the step of calculating a stroke volume as a function of the calibrated indice and as a function of the extracted data. The calculated stroke volume can be calculated for monitoring and tracking changes. The extracted pulse wave analysis data can comprise:
- a diastolic pressure,
- a pressure at an inflection point during systole, the at least one time interval can comprise a systolic time, the calculated stroke volume being preferably calculated as a function of:

$$(Pi-DAP)*ST,$$

where DAP is the diastolic pressure, Pi is the pressure at the inflection point during systole, and ST is the systolic time. The indice of arterial stiffness can be a characteristic impedance, the calculated stroke volume being preferably calculated according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time. The indice of arterial stiffness can be a total arterial compliance or a total arterial stiffness, the at least one time interval can further comprise a time to the pressure at the inflection point during systole, the calculated stroke volume being preferably calculated according to the following equation:

$$SV=C_{cal}*[(Pi-DAP)*ST/\Delta t],$$

where $C_{cal}$ is the calibrated total arterial compliance that is equal to the inverse of the calibrated total arterial stiffness $1/C_{cal}$, DAP is the diastolic pressure, Pi is the pressure at the inflection point during systole, SV is the calculated stroke volume, ST is the systolic time, and Δt is the time to the pressure at the inflection point during systole.

An other aspect of the invention concerns a process for calculating a stroke volume, comprising the step of extracting pulse wave analysis data from a recorded pressure of an artery, the process being characterized in that the recorded pressure is recorded as a function of time, the stroke volume being calculated as a function of the extracted data, the extracted pulse wave analysis data comprising at least one time interval. Thus, the stroke volume is calculated as a function of the at least one time interval.

The extracted pulse wave analysis data can comprise at least one pressure. Thus, in this case, the stroke volume is calculated as a function of the at least one pressure.

The calculated stroke volume can be calculated for monitoring and tracking changes.

The extracted pulse wave analysis data can comprise:
- a diastolic pressure,
- a pressure at an inflection point during systole, the at least one time interval can comprise a systolic time, the calculated stroke volume being preferably calculated as a function of:

$$(Pi-DAP)*ST.$$

where DAP is the diastolic pressure, Pi is the pressure at the inflection point during systole, and ST is the systolic time.

The calculated stroke volume is preferably calculated as a function of a calibrated indice of arterial stiffness and as a function of the extracted data. Thus, the process for calculating a stroke volume according to this invention can comprise a calibration of the indice of arterial stiffness, the calibration comprising preferably a step of arbitrarily fixing the value of the calibrated indice of arterial stiffness, or a step of setting the calibration with a previous calculation of the indice.

The indice of arterial stiffness can be a characteristic impedance, the calculated stroke volume being preferably calculated according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time.

The indice of arterial stiffness can be a total arterial compliance or a total arterial stiffness, the at least one time interval can further comprise a time to the pressure at the inflection point during systole, the calculated stroke volume being preferably calculated according to the following equation:

$$SV=C_{cal}*[(Pi-DAP)*ST/\Delta t]$$

where $C_{cal}$ is the calibrated total arterial compliance that is equal to the inverse of the calibrated total arterial stiffness $1/C_{cal}$, DAP is the diastolic pressure, Pi is the pressure at the inflection point during systole, SV is the calculated stroke volume, ST is the systolic time, and Δt is the time to the pressure at the inflection point during systole.

An other aspect of the invention concerns a device for calculating an indice of arterial stiffness, comprising:
- means for extracting pulse wave analysis data from a recorded pressure of an artery, the recorded pressure being recorded as a function of time,
- means for calculating the indice of arterial stiffness as a function of the extracted data, the extracted pulse wave analysis data comprising at least one time interval.

The extracted pulse wave analysis data can comprise at least one pressure.

The at least one time interval can comprise a systolic time, the means for calculating the indice of arterial stiffness being arranged for calculating the indice as a function of the systolic time.

The at least one time interval can comprise a time to the pressure at an inflection point during systole, the means for calculating the indice of arterial stiffness being preferably arranged for calculating the indice as a function of the ratio:

$$ST/\Delta t,$$

where $\Delta t$ is the time to the pressure at the inflection point during systole and ST is the systolic time.

The at least one time interval can comprise a period of the artery, the means for calculating the indice of arterial stiffness being preferably arranged for calculating the indice as a function of the ratio:

$$ST/T,$$

where T is the period and ST is the systolic time.

The device for calculating an indice of arterial stiffness according to the invention can further comprises means for recording a stroke volume, the means for calculating the indice of arterial stiffness being preferably arranged for calculating the indice as a function of the recorded stroke volume.

The extracted pulse wave analysis data can comprise:
  a diastolic pressure,
  a pressure at an inflection point during systole,
the means for calculating the indice of arterial stiffness being preferably arranged for calculating the indice as a function of the following ratio:

$$[Pi-DAP]/SV,$$

where DAP is the diastolic pressure, Pi is the pressure at the inflection point during systole, and SV is the recorded stroke volume. The at least one time interval can comprise a systolic time and the means for calculating the indice of arterial stiffness are preferably arranged for calculating the indice as a function of the following ratio:
[(Pi-DAP)*ST]/SV, where DAP is the diastolic pressure, Pi is the pressure at the inflection point during systole, SV is the recorded stroke volume, and ST is the systolic time. The at least one time interval can comprise a time to the pressure at the inflection point during systole, and the means for calculating the indice of arterial stiffness are preferably arranged for calculating the indice as a function of the following ratio:

$$[(Pi-DAP)*ST]/(SV*\Delta t),$$

where DAP is the diastolic pressure, Pi is the pressure at the inflection point during systole, SV is the recorded stroke volume, ST is the systolic time, and $\Delta t$ is the time to the pressure at the inflection point during systole.

The indice of arterial stiffness can be a characteristic impedance. In this case, the extracted pulse wave analysis data can comprise:
  a diastolic pressure,
  a pressure at an inflection point during systole,
the at least one time interval can comprise a systolic time, and the means for calculating the indice of arterial stiffness are preferably arranged for calculating the characteristic impedance according to the following equation:

$$Zc=[(Pi-DAP)*ST]/(2SV),$$

where Zc is the characteristic impedance, DAP is the diastolic pressure, Pi is the pressure at the inflection point during systole, SV is a recorded stroke volume, and ST is the systolic time.

The indice of arterial stiffness can be a total arterial compliance. In this case, the extracted pulse wave analysis data can comprise:
  a diastolic pressure,
  a pressure at an inflection point during systole,
the at least one time interval can comprise a systolic time and a time to the pressure at the inflection point during systole, and the means for calculating the indice of arterial stiffness are preferably arranged for calculating the total arterial compliance according to the following equation:

$$C=(SV*\Delta t)/[(Pi-DAP)*ST],$$

where C is the total arterial compliance, DAP is the diastolic pressure, Pi is the pressure at the inflection point during systole, SV is a recorded stroke volume, ST is the systolic time, and $\Delta t$ is the time to the pressure at the inflection point during systole.

The indice of arterial stiffness can be a total arterial stiffness. In this case, the extracted pulse wave analysis data can comprise:
  a diastolic pressure,
  a pressure at an inflection point during systole,
the at least one time interval can comprise a systolic time and a time to the pressure at the inflection point during systole, and the means for calculating the indice of arterial stiffness are preferably arranged for calculating the total arterial stiffness according to the following equation:

$$1/C=[(Pi-DAP)*ST]/(SV*\Delta t),$$

where 1/C is the total arterial stiffness, DAP is the diastolic pressure, Pi is the pressure at the inflection point during systole, SV is a recorded stroke volume, ST is the systolic time, and $\Delta t$ is the time to the pressure at the inflection point during systole.

The indice of arterial stiffness can be a waveguide function. In this case, the extracted pulse wave analysis data can comprise:
  a diastolic pressure,
  a pressure at an inflection point during systole,
  a mean aortic pressure,
  a mean downstream pressure
the at least one time interval can comprise a systolic time and a period of the artery, and the means for calculating the indice of arterial stiffness are preferably arranged for calculating the waveguide function according to the following equation:

$$Zc/Rs=[(Pi-DAP)/(MAP-Po)]*[(ST)/(2T)],$$

where Zc/Rs is the waveguide function, DAP is the diastolic pressure, Pi is the pressure at the inflection point during systole, ST is the systolic time, T is the period, MAP is the mean aortic pressure and Po is the mean downstream pressure.

The device for calculating an indice of arterial stiffness according to the invention can further comprise means for calibrating the indice of arterial stiffness, the calibration means being arranged for setting the calibration of the indice of arterial stiffness with a calculation of the indice implemented by the means for calculating the indice of arterial stiffness, the device further comprising means for calculating a stroke volume as a function of the calibrated indice and as a function of the extracted data. The means for calculating a stroke volume can be arranged for monitoring and tracking changes. The extracted pulse wave analysis data can comprise:

a diastolic pressure,
a pressure at an inflection point during systole,
the at least one time interval can comprise a systolic time, the means for calculating a stroke volume being preferably arranged for calculating the stroke volume as a function of:

$$(Pi-DAP)*ST,$$

where DAP is the diastolic pressure, Pi is the pressure at the inflection point during systole, and ST is the systolic time. The indice of arterial stiffness can be a characteristic impedance, the means for calculating a stroke volume being preferably arranged for calculating the stroke volume according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time. The indice of arterial stiffness can be a total arterial compliance or a total arterial stiffness, the at least one time interval can further comprise a time to the pressure at the inflection point during systole, the means for calculating a stroke volume being preferably arranged for calculating the stroke volume according to the following equation:

$$SV=C_{cal}*[(Pi-DAP)*ST/\Delta t],$$

where $C_{cal}$ is the calibrated total arterial compliance that is equal to the inverse of the calibrated total arterial stiffness $1/C_{cal}$, DAP is the diastolic pressure, Pi is the pressure at the inflection point during systole, SV is the calculated stroke volume, ST is the systolic time, and $\Delta t$ is the time to the pressure at the inflection point during systole.

An other aspect of the invention concerns a device for calculating a stroke volume, comprising means for extracting pulse wave analysis data from a recorded pressure of an artery, the recorded pressure being recorded as a function of time, and means for calculating the stroke volume as a function of the extracted data, the extracted pulse wave analysis data comprising at least one time interval.

The extracted pulse wave analysis data can comprise at least one pressure.

The means for calculating a stroke volume can be arranged for monitoring and tracking changes.

The extracted pulse wave analysis data can comprise:
a diastolic pressure,
a pressure at an inflection point during systole,
the at least one time interval can comprise a systolic time, the means for calculating a stroke volume being preferably arranged for calculating the stroke volume as a function of:

$$(Pi-DAP)*ST,$$

where DAP is the diastolic pressure, Pi is the pressure at the inflection point during systole, and ST is the systolic time.

The means for calculating a stroke volume can be arranged for calculating the stroke volume as a function of a calibrated indice of arterial stiffness and as a function of the extracted data. Thus, the device for calculating a stroke volume according to this invention can comprise means for calibrating the indice of arterial stiffness; the calibration means being preferably arranged for arbitrarily fixing the value of the calibrated indice of arterial stiffness, or being arranged for setting the calibration of the indice of arterial stiffness with a previous calculation of the indice implemented by means for calculating the indice of arterial stiffness.

The indice of arterial stiffness can be a characteristic impedance, the means for calculating a stroke volume being preferably arranged for calculating the stroke volume according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time.

The indice of arterial stiffness can be a total arterial compliance or a total arterial stiffness, the at least one time interval can further comprise a time to the pressure at the inflection point during systole, the means for calculating a stroke volume being preferably arranged for calculating the stroke volume according to the following equation:

$$SV=C_{cal}*[(Pi-DAP)*ST/\Delta t],$$

where $C_{cal}$ is the calibrated total arterial compliance that is equal to the inverse of the calibrated total arterial stiffness $1/C_{cal}$, DAP is the diastolic pressure, Pi is the pressure at the inflection point during systole, SV is the calculated stroke volume, ST is the systolic time, and $\Delta t$ is the time to the pressure at the inflection point during systole.

BRIEF DESCRIPTION OF THE DRAWINGS

Other advantages and characteristics of the invention will appear upon examination of the detailed description of embodiments which are no way limitative, and of the appended drawings in which.

DETAILED DESCRIPTION

Referring to FIGS. 1 to 6, a device according to the invention implementing a process according to the invention will now be described.

Total arterial stiffness plays a contributory role throughout aging and in numerous cardiovascular diseases, including hypertension. Aortic stiffening is responsible for an increased characteristic impedance (ie, the impedance to the left ventricular pulsatile flow), thus increasing the forward pressure-wave amplitude that contributes to pulse pressure elevation. Aortic stiffening also increases pulse wave velocity, and this results in anticipated and enhanced wave reflections, further augmenting central pulse pressure. Unfortunately, there is no simple time-domain estimate of characteristic impedance. Furthermore, recent guidelines have reviewed the limitations of diastolic pulse contour analysis to estimate arterial stiffness in the time domain.

The present invention proposes that systolic pulse contour analysis may provide new, simple time-domain indices quantifying pulsatile load in resting humans. Our proposal was mainly based on two simple, validated assumptions:

(1) a linear aortic pressure-flow relationship in early systole and (2) a triangular aortic flow wave during systole.

This allows us to describe new time domain estimates of characteristic impedance, pulsatile load (waveguide ratio), total arterial compliance, and total arterial stiffness. It is demonstrated that total arterial stiffness may be estimated by the following formula:

$$[(Pi-DAP)*ST]/(SV*\Delta t),$$

where Pi is the aortic pressure at the inflection point 7 (peak forward pressure wave) during early systole, DAP is diastolic aortic pressure, ST is systolic ejection time, SV is stroke volume, and $\Delta t$ is the time-to-Pi. A mathematical relationship among time intervals and indices of pulsatile load is demonstrated, and the clinical implications are discussed in terms of cardiovascular risk and stroke volume prediction.

In the equations of this document, / is the division operator and * is the multiplication operator.

In the first part of this description, we will briefly summarize how current hemodynamic theory explains the various components of aortic pressure pulse and arterial load in resting humans.

In the second part of the description, we will propose that systolic pulse contour analysis may provide new, simple time-domain indices quantifying characteristic impedance (Zc), total arterial compliance (C), total arterial stiffness (1/C), and the so-called "waveguide" function in humans. Our proposal will be mainly based on two simple, validated assumptions: (1) a linear aortic pressure-flow relationship in early systole and (2) a triangular aortic flow wave during systole. The limitations of our approach will be discussed. Finally, the clinical implications of the proposed new indices will be discussed.

Arterial Hemodynamics
Aortic Pressure

Figure 1:
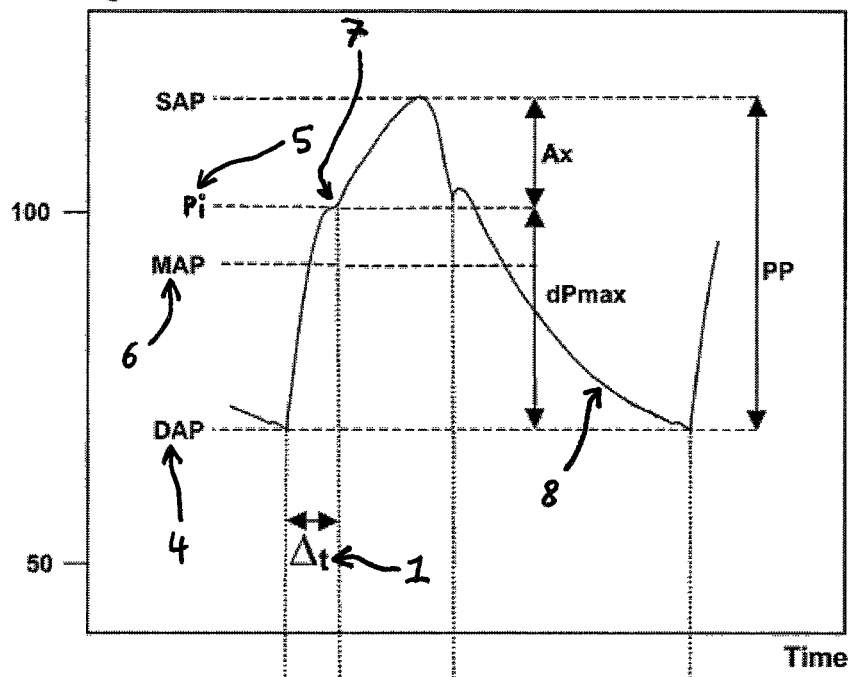
FIG. 1 is a schematic representation of aortic pressure (top) and aortic flow (bottom) as a function of time, where:
SAP is the systolic aortic pressure;
DAP is the diastolic aortic pressure;
MAP is the mean aortic pressure;
PP is the aortic pulse pressure;
Pi is the pressure at the inflection point during early systole;
dPmax is the peak forward pressure (dPmax=Pi−DAP);
Ax is the augmentation pressure (Ax=SAP−Pi);
$\Delta t$ is the time-to-Pi;
ST is the systolic time;
T is the heart period.
Figure 1:
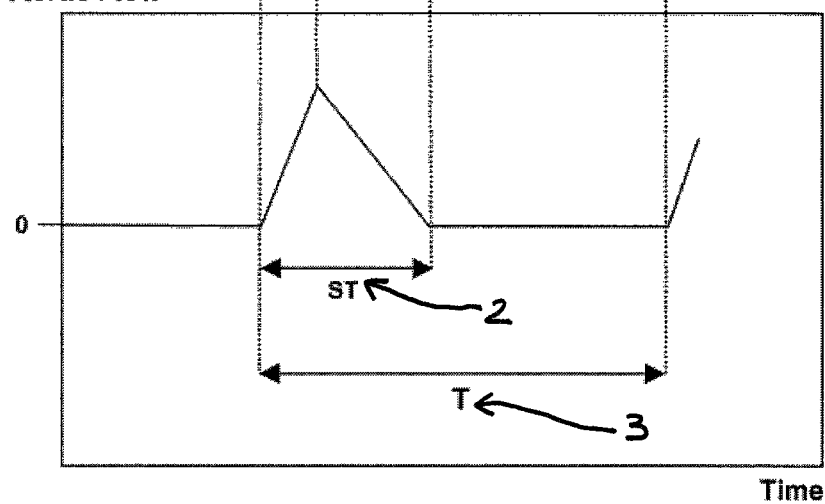
Figure 2:
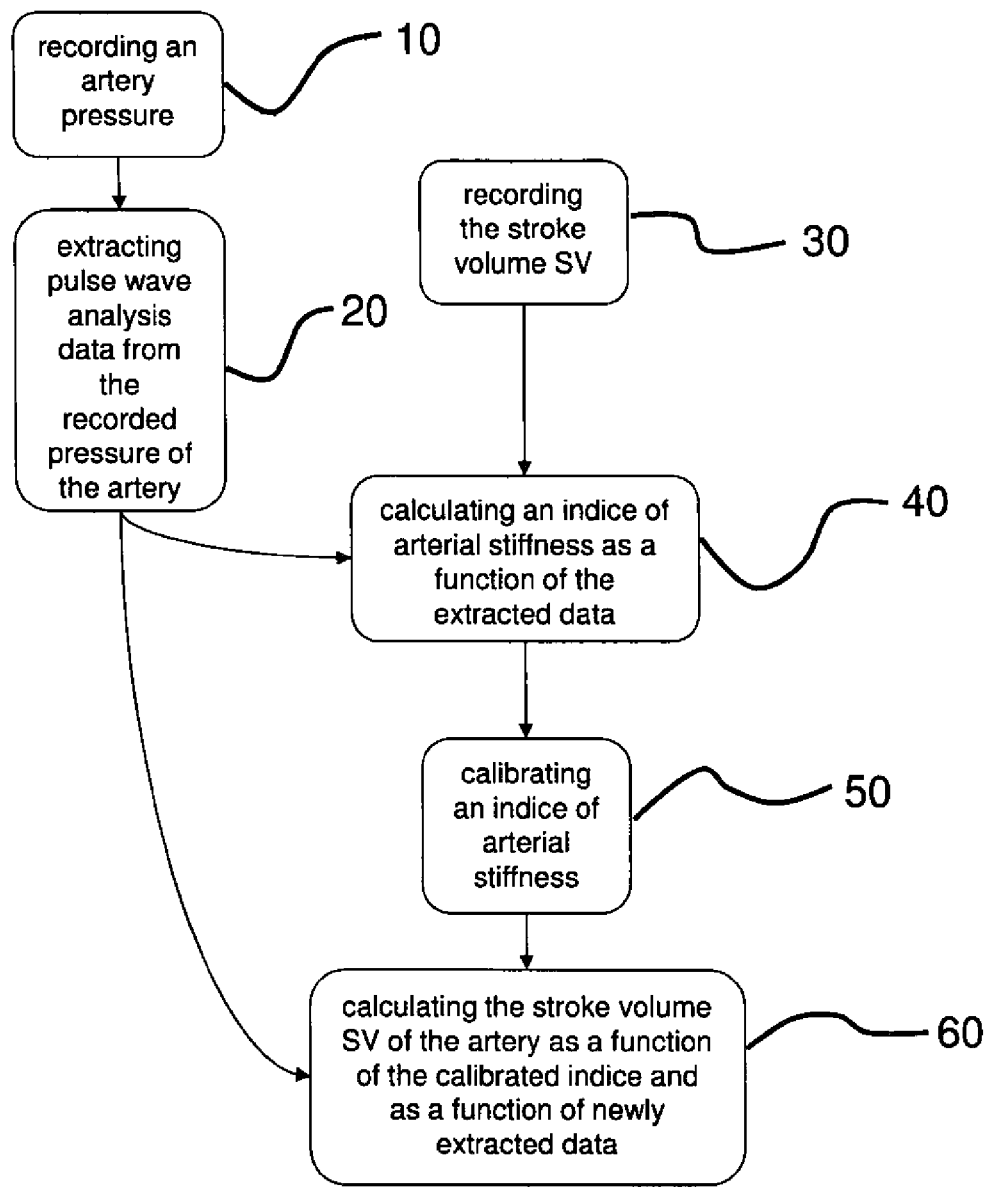
FIGS. 2 and 3 are schematic representations of a first embodiment of a process according to the invention.
Figure 3:
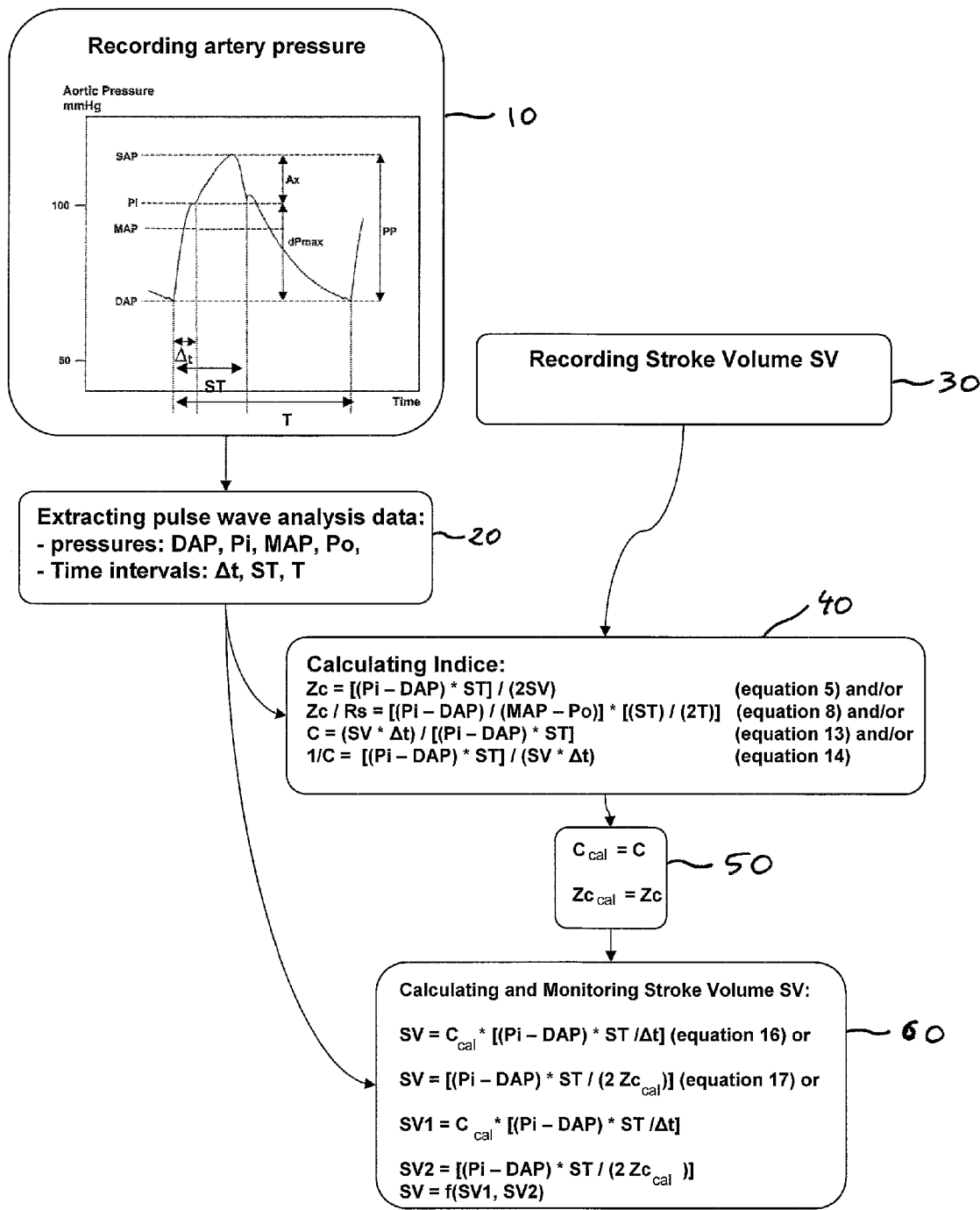
Figure 4:
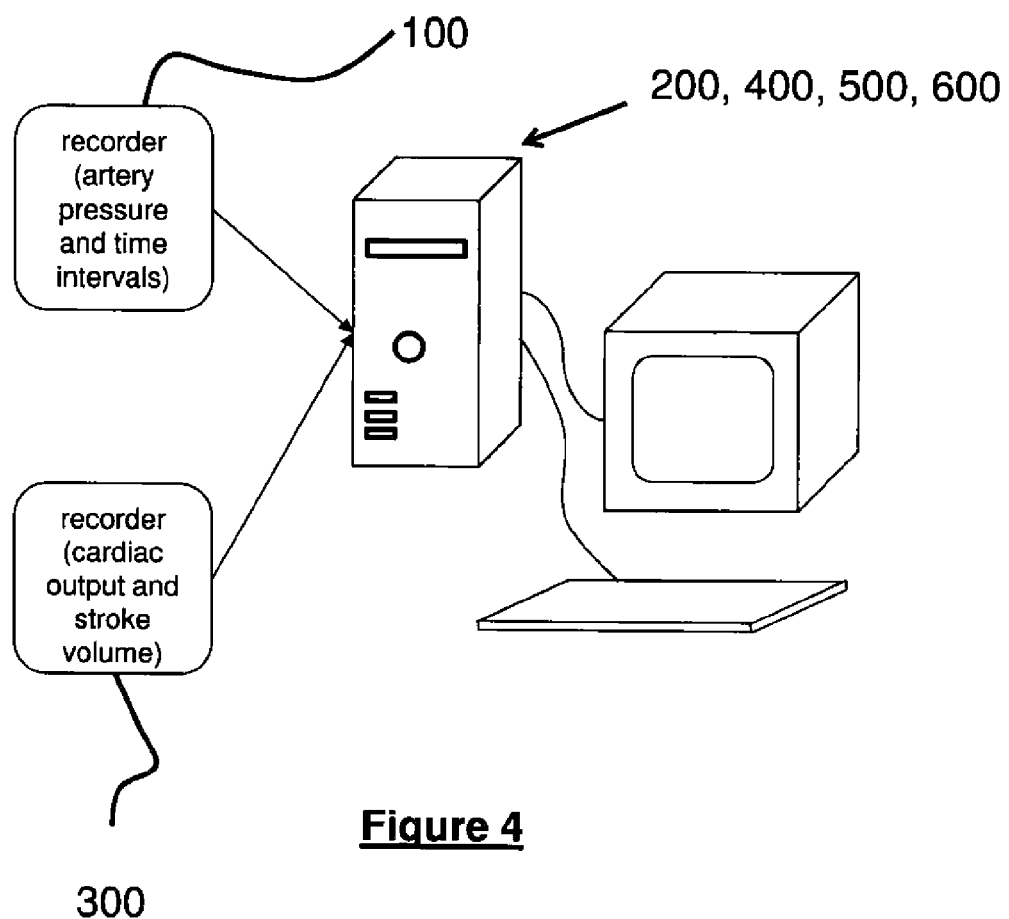
FIG. 4 is a schematic representation of a device according to the invention implementing the first embodiment of a process according to the invention.

Mean aortic pressure (MAP) is the steady component of aortic pressure, while systolic (SAP) and diastolic (DAP) aortic pressures help quantify the pulsatile component of aortic pressure, namely pulse pressure (PP=SAP−DAP) (FIG. 1). From the foot of the systolic pressure wave to the peak systolic pressure wave, two components can be distinguished: the peck forward pressure wave (dPmax) and the augmentation pressure (Ax) (ie, the amplitude of the reflected pressure wave). An inflection point allows separating these 2 components, and the pressure at the inflection point (Pi) indicates the beginning upstroke of the reflected wave [7, 8]. The time to the peak/shoulder of the first pressure wave component during systole ($\Delta t$) quantifies the timing of the pressure wave reflection. In healthy young individuals, Ax is low and weakly contributes to PP. The reflected pressure wave is rather diffuse and maintains a relatively high aortic pressure in early diastole, thus boosting coronary artery filling. In elderly individuals, the reflected pressure wave is increased and narrowed, thus significantly contributing to PP (high Ax value) rather than increasing early diastolic pressure. Increased arterial stiffness of the aorta and proximal large arteries is related to the aging process.

The widening of PP is the consequence of alterations of large artery structure and function related to cardiovascular risk factors. Cardiovascular risk factors are known to favor and accelerate the atherosclerotic process, and the widening of PP is involved in the cardiovascular consequences of aging and in the development of cardiovascular diseases, especially hypertension [1-6].

Hydraulic Load

The hydraulic load opposing to ejection consists of a steady component composed of systemic vascular resistance (Rs) and a pulsatile component consisting of distributed compliant and inertial properties [9-12]. The steady and pulsatile components of arterial load are dependent on distal and proximal portions of the systemic vascular tree, respectively, and may be controlled and modified separately.

Physicians are familiar with the concept of Rs, which is a measure of the extent to which the systemic circulation "resists" to mean cardiac output. The driving pressure is the MAP minus the mean downstream pressure. The driving pressure is related to the viscous (frictional) resistance of the blood when flow is induced. The Rs is calculated by dividing the driving pressure by cardiac output. The architecture and function of the microvascular network are the primary determinants of Rs.

In hydraulic circuit when the flow is pulsatile, the relationship between pulsatile flow and pulsatile pressure includes not only the opposition to flow afforded by friction but also due to both the vascular elasticity and the inertia of blood mass. Because blood is incompressible and given that the proximal aorta and its major branches are viscoelastic vessels, the blood volume ejected by the left ventricle and entering the circuit is accommodated thanks to aortic dilatation during systole. The compliance of the proximal aorta and large arteries mainly depends on the relative contribution of elastin and collagen [1-5]. Total arterial compliance (C) is a measure of the capacity of the arterial system to accommodate this sudden increase in volume. The major part of the stroke volume is stored in the compliant proximal aorta, which is equivalent to charging a capacitor in electronics, and then released during diastole [13].

In cases where the measurement of stroke volume is available, various estimates of C may be obtained by diastolic pulse contour analysis using analogies with electrical models of the systemic circulation. Various methods have been proposed to estimate C in diastole, including the time decay method, the area method, and other methods using a modified windkessel analog [13-17]. Recent guidelines have reviewed the theoretical, technical, and practical limitations of such methods [6]. From a theoretical point of view, the pure RC windkessel model is zero-dimensional, and implies infinite pulse wave velocity. Because the windkessel model does not take into account the finite pulse wave velocity and the phenomena of blood propagation and wave reflections, the model does not apply at high frequency and during the systolic period. However, it must be noted that the windkessel model applies in diastole whatever the model chosen for the overall systemic circulation, namely pure windkessel model, distributed linear model, or nonlinear model [9-12].

In fact, pulse wave velocity has finite values, and this implies finite values of travel times (forward and backward) such that a more realistic propagative model must be used in systole [9-12]. According to the transmission line theory, the distributed linear model emphasizes the importance of pulse wave velocity, wave reflections, and characteristic impedance (ie, the input impedance in the absence of wave reflection). The distributed linear model takes into account the fact that pressure waves travel along the aorta with finite velocity and may suffer attenuation and experience reflection, resulting in backward propagating waves that in turn influence the aortic pressure and flow curve. Although the windkessel model assumes that all the reflections occur immediately, the distributed linear model takes into account the time delay of the reflections with respect to the initial wavefront.

Characteristic Impedance (Zc) and the Waveguide Function

Characteristic impedance governs the pressure-flow relationship in the proximal aorta until the arrival of the first pressure wave reflection. Characteristic impedance may be expressed as the square root of the L/C ratio, where L is blood inertance [10]. Decreased C (ie, stiffening of the aorta) is thus a major cause of increased Zc.

In a normal aorta, Zc is a small fraction (5% to 10%) of Rs, and this "impedance mismatch" has two main consequences. First, the heart and vessels are thus properly matched or coupled, and the aorta functions as a low impedance interface or waveguide that serves to isolate pulsatile output of the heart at one end from the high resistance vessels at the other [18]. Second, the impedance mismatch together with multiple bifurcation and finite length of the network is responsible for wave reflections.

Indeed, pressure and flow measured in the aorta result from waves traveling simultaneously from heart to periphery (forward wave) and in the retrograde direction (backward wave) with finite velocity [9-12]. It is widely admitted that pressure increases when forward pressure wave from the heart collides with the backward (reflected) pressure wave. Conversely, when forward flow wave collides with the backward traveling flow wave, flow decreases. Because forward and backward waves have either the same (positive) sign (pressure) or have opposite signs (flow), the result of more wave reflections is decreased resemblance of measured aortic flow and measured aortic pressure. Conversely, in cases where wave reflections are negligible (eg, as observed in the pulmonary artery of healthy subjects), central pressure and flow waves look alike [8]. Wave reflections explain why the modulus magnitude and phase shift of the impedance spectra varies with frequency [7-12]. The timing and extent of wave reflections mainly depend on reflection coefficient (determined by Zc and Rs), functional length of the arterial network, pulse wave velocity, and heart rate [1, 6, 10-12].

The Zc is most often calculated in the frequency domain, which requires simultaneous high-fidelity pressure and flow recordings, sophisticated mathematical calculations, and a number of theoretical assumptions (including hemodynamic stability) that are not always fulfilled in clinics [10, 11]. However, thanks to a number of reasonable approximations, it has been assumed that Zc may be considered as real and frequency independent. Simpler, time-domain calculation methods of Zc have been validated in previous invasive studies [19, 20] and have proved useful in pathophysiological, noninvasive studies [21, 22]. It is accepted that the ratio of the peak forward pulsatile pressure to the peak flow is a reliable estimate of Zc, but precise flow velocity recordings are still required and this limits a more widespread use of the method.

Functional Measures of Arterial Stiffness: Zc and Pulse Wave Velocity (PWV)

Aortic stiffening is responsible for an increased impedance to the left ventricular pulsatile flow (Zc), increasing the forward pressure-wave amplitude (dPmax) that contributes to PP elevation. Aortic stiffening also increases PWV, and higher PWV results in anticipated and enhanced wave reflections, further augmenting central systolic pressure and PP by increasing the contribution of Ax [1-7].

A number of papers and guidelines have previously addressed the theoretical, methodological, and practical issues related to the estimation of arterial stiffness [1-6]. Theory indicates that both Zc and PWV are dependent on the caliber and compliant properties of the aorta and first large arterial branches. Zc and PWV are thus viewed as functional measures of large artery stiffness. Calculating Zc requires simultaneous pressure-flow recordings and clinically relevant indices, allowing the simple quantification of Zc are still lacking. Although PWV is fast and easy to obtain, several limitations have been underlined, including difficulties and inaccuracies in the measurement of the distance covered by the pulse waves [6]. Furthermore, Zc is five times as sensitive to changes in vessel radius as PWV. It has been suggested that Zc is more sensitive to the endothelium-mediated changes in vessel diameter; therefore, is more amenable than PWV to short-term regulation [3, 18]. As a result, simple method allowing Zc estimation is especially needed in practice.

New Estimates of Pulsatile Arterial Load by Using Systolic Pulse Contour Analysis Referring to FIGS. 1 to 4, a first embodiment of a process according to the invention for calculating an indice of arterial stiffness and/or a stroke volume by using systolic pulse contour analysis comprises:

a step 10 of recording an artery pressure, the recorded pressure being recorded as a function of time and being illustrated in FIG. 1, the recorded pressure being recorded as a function of time by means 100 for recording an artery pressure and time intervals; and a subsequent step 20 of extracting pulse wave analysis data from the recorded pressure of the artery, the pulse wave analysis data being extracted by means 200 for extracting pulse wave analysis data.

The recorded pressure is roughly periodic. FIG. 1 illustrates one pressure cycle of the artery, that is the pressure of the artery over one period T. Each cycle or period of the recorded pressure comprises a first part called systole during time interval ST, and a subsequent part called diastole. The means 100 for recording an artery pressure (preferably the central aortic pressure) and time intervals may be non-invasive or invasive as follows:

1) Non-invasive:
   radial artery tonometry
   carotid artery tonometry
   external pressure transducer applied at the suprasternal level or cat the carotid artery level
   oscillometric devices (assuming empirical corrections for pulse wave amplification)
   photoplethysmography, including digital and ear photoplethysmography (assuming corrections for pulse wave amplification)
   pulse oxymetry, including digital and ear pulse oxymetry (assuming corrections corrections for pulse wave amplification).
   Doppler-derived aortic pressures and left-sided time intervals
   Doppler-derived pulmonary artery pressures and right-sided time intervals.

2) Invasive:
   Fluid-filled aortic catheter
   Fluid-filled catheters in the femoral artery, brachial artery, radial artery (assuming corrections for pulse wave amplification).
   Fluid-filled pulmonary artery catheter
   Micromanometer in the aorta
   Micromanometer in the pulmonary artery The means 200 of extracting pulse wave analysis data (like Pi, DAP, T, ST, Δt, . . . shown in FIG. 1) from the recorded artery pressure may be arranged to implement:
   Computerized data analysis
   Automated shape recognition
   Manual analysis
   Semi-automated methods with various combinations of each three previous methods.

The time intervals T, ST, Δt can also be extracted by using a electrocardiogram EKG method or a phonocardiogram method. The means 200 of extracting pulse wave analysis data can comprise a computer, a microprocessor, a digital circuit or an analogical circuit. The means of extracting can comprise an input arranged to receive the artery pressure recorded by the means 100 for recording an artery pressure as a function of time previously described.

The extracted pulse wave analysis data comprise at least one pressure among DAP, Pi, MAP, and Po.

Furthermore, the extracted pulse wave analysis data comprise at least one time interval among ST, T, and Lt.

Characteristic Impedance

As previously discussed, the peak amplitude (dPmax) of the forward aortic pressure wave may be approximated as follows (FIG. 1):

$$dPmax=Pi-DAP \quad \text{(equation 1)}$$

The concept of characteristic impedance implies that the pressure-flow relationship is linear in the proximal aorta when aortic pressure is measured before the arrival of the first reflected wave [9-12, 19, 20]. Previous studies [19-22] have taken advantage of such an assumption to calculate Zc in the time-domain as the ratio of the peak amplitude of the forward aortic pressure wave (dPmax) divided by the peak pulsatile flow (Qmax):

$$Zc=dPmax/Qmax \quad \text{(equation 2)}$$

On the other hand, the left ventricular pulsatile outflow results in a systolic flow wave in the proximal aorta that may be described by using a triangular shape [10, 11, 23]. The accuracy of such an approximation has been recently discussed and has proved useful to provide a reasonable estimate of pulsatile flow [24]. Because there is flow in the proximal aorta only during the systolic period, we obtain:

$$Q=(Qmax*ST)/(2T) \quad \text{(equation 3)}$$

where Q is the mean cardiac output, T is the heart period, and ST is systolic time (ejection duration or left ventricular ejection time). Finally, Q may be expressed as follows:

$$Q=SV/T \quad \text{(equation 4)}$$

where SV is stroke volume. SV is the ventricular stroke volume: SV is the mean stroke volume ejected by either the left or the right ventricle per beat.

By combining equations 1-4 we obtain:

$$Zc = [(Pi-DAP)*ST]/(2SV)$$
$$Zc = \frac{(Pi-DAP)ST}{2SV} \quad \text{(equation 5)}$$

It is therefore suggested that pulse contour analysis may provide a valuable estimate of Zc. As compared to previous time-domain methods for Zc calculation, solving equation 5 does not require continuous flow velocity recordings and is thus applicable to patients whose mean cardiac output is monitored by using either invasive (eg, thermodilution) or noninvasive (eg, Doppler echocardiography) validated techniques.

The Waveguide Ratio

In most clinical situations, Q is not available, making it impossible to calculate Zc. Nevertheless, in such conditions, the waveguide function of the aorta [18] may still be calculated. Indeed, the systemic vascular resistance is calculated as:

$$Rs=(MAP-Po)/Q \quad \text{(equation 6)}$$

where MAP is mean aortic pressure and Po is the mean downstream pressure. Thus, the pulsatile arterial load relative to steady load (waveguide ratio) is obtained as follows:

$$Zc/Rs=[(Pi-DAP)*ST]/[(MAP-Po)*2T] \quad \text{(equation 7)}$$

Put differently we obtain $$Zc/Rs = [(Pi-DAP)/(MAP-Po)]*[(ST)/(2T)] \quad \text{(equation 8)}$$
$$\frac{Zc}{Rs} = \frac{(Pi-DAP)}{(MAP-Po)} \frac{ST}{2T}$$

Thus the waveguide ratio may be simply calculated as the product of a pressure ratio and a time ratio.

It must be noted that the waveguide ratio is critically related to the ejection time over heart period ratio (ST/T), namely the "duty cycle" (or "duty ratio"). By analogy with engines, the duty cycle may be viewed as the fraction of time the "system" (ie, the left ventricle) is actually employed in performing its systolic function (ie, ejection). To the best of our knowledge, the duty cycle has not been extensively studied so far in humans. It has been recently demonstrated that prolonged ejection duration after beta-adrenergic blocking agents [25] and in patients with diastolic dysfunction [26] may compromise the left ventricle-vascular coupling by allowing more time for the reflected pressure wave to peak during systole at the aortic level and to increase the afterload of the still-ejecting left ventricle.

One result of the waveguide ratio is that it provides a physiological estimate of the relative pulsatile load put on the heart, as reflected in the Zc/Rs ratio. Another is that it does not require any measurement of cardiac output and thus may be derived from aortic pressure recordings only. Further studies are needed to test this ratio and its correlates in both health and disease.

Total Arterial Compliance (C) and Stiffness (1/C)

In an attempt to obtain a clinically usable estimate of total arterial stiffness (1/C), a distributed linear model of the systemic circulation may be used together with a number of reasonable and simplified assumptions including: (1) that Rs, L, and C are constant and independent of the frequency, (2) that the aorta may be described as one uniform tube of effective length l, thereby neglecting the effects of tapering and bifurcation, (3) that the phase and group wave propagation velocities are identical, constant (PWV), and independent of the frequency (ie, there is no dispersion). The PWV may be expressed as a function of L and C and the time from systolic pressure upstroke to the pressure inflection point 7 indicating pressure reflection (Δt) may be expressed as a function of the effective forward and backward travelling distance [10]. Thus we obtain:

$$PWV=l/\text{sqrt}(LC) \quad \text{(equation 9)}$$

$$\Delta t=2l/PWV=2\text{sqrt}(LC) \quad \text{(equation 10)}$$

On the other hand, Zc may be expressed as a function of L and C:

$$Zc=\text{sqrt}(L/C) \quad \text{(equation 11)}$$

By combining equations 10 and 11 we obtain $$C=\Delta t/2Zc \quad \text{(equation 12)}$$

By combining equations 5 and 12 we obtain $$C = (SV * \Delta t)/[(Pi - DAP) * ST] \quad \text{(equation 13)}$$
$$C = \frac{SV \Delta t}{(Pi - DAP)ST}$$

$$1/C = [(Pi - DAP) * ST]/(SV * \Delta t) \quad \text{(equation 14)}$$
$$\frac{1}{C} = \frac{(Pi - DAP)ST}{SV \Delta t}$$

the total arterial compliance C being equal to the inverse of the total arterial stiffness 1/C. Thus, from a theoretical point of view, equations 13 and 14 provide new, simple estimates of total arterial compliance and stiffness in the time domain using systolic pulse contour analysis. Some authors have suggested that a fixed 30% to 33% $\Delta t$/ST value may be on average correct in most resting subjects [24, 27]. Other authors have highlighted the importance of considering subtle differences in the $\Delta t$/ST value in clinical studies performed in both health (eg, throughout aging) and disease [7, 8, 11, 23]. Further experimental studies are needed to test the validity of these formulae.

The first embodiment of a process according to the invention further comprises the step 40 of calculating an indice of arterial stiffness as a function of the extracted data. The indice of arterial stiffness is calculated by calculation means 400. The indice of arterial stiffness is comprised in the group consisting of the characteristic impedance Zc, the total arterial compliance C, the total arterial stiffness 1/C, and the waveguide function Zc/Rs.

The extracted data depends on which indice of arterial stiffness is calculated.

The extracted data comprise:
the time $\Delta t$ to the pressure at an inflection point 7 during early systole, this time $\Delta t$ being referenced 1 in FIG. 1, if the calculated indice of arterial stiffness is the total arterial compliance C or the total arterial stiffness 1/C;
the systolic time ST, referenced 2 in FIG. 1, if the calculated indice of arterial stiffness is the characteristic impedance Zc or the total arterial compliance C or the total arterial stiffness 1/C or the waveguide function Zc/Rs;
the artery pulse period T, referenced 3 in FIG. 1, if the calculated indice of arterial stiffness is the waveguide function Zc/Rs; in the case of the heart, the artery pulse period T is the heart period;
the diastolic pressure DAP, referenced 4 in FIG. 1, if the calculated indice of arterial stiffness is the characteristic impedance Zc or the total arterial compliance C or the total arterial stiffness 1/C or the waveguide function Zc/Rs;
the pressure Pi at the inflection point 7 during early systole, this pressure Pi being referenced 5 in FIG. 1, if the calculated indice of arterial stiffness is the characteristic impedance Zc or the total arterial compliance C or the total arterial stiffness 1/C or the waveguide function Zc/Rs;
the mean aortic pressure MAP, referenced 6 in FIG. 1, if the calculated indice of arterial stiffness is the waveguide function Zc/Rs;
the mean downstream pressure Po, if the calculated indice of arterial stiffness is the waveguide function Zc/Rs; Po is not showed in FIG. 1, and is the theoretical artery pressure if the stroke volume SV was equal to zero (typically 5 to 30 mm Hg); in other words, Po is equal to the asymptote of the exponential decay 8 of aortic pressure in diastole; Po is typically estimated and calculated by fitting the exponential decay of aortic pressure in diastole (e.g., using best-fit method or derivative method); in another realization mode, the value of Po is not extracted from the recorded pressure, but is fixed arbitrarily.

If the calculated indice of arterial stiffness is the characteristic impedance Zc or the total arterial compliance C or the total arterial stiffness 1/C, the first embodiment of a process according to the invention further comprises, before the calculating step 40, the step 30 of recording the stroke volume SV of the artery whose pressure has been previously recorded in step 10. The stroke volume SV is recorded by means 300 for recording cardiac output and stroke volume.

The means 400 for calculating Zc, C, 1/C, and waveguide ratio may be as follows:
standard calculations according to equations 5, 8, 13, 14.

The means 400 of calculating can comprise a computer, a microprocessor, a digital circuit or an analogical circuit. Means of calculating 400 can comprise an input arranged to receive the analysis data extracted by the extracting means 200 and to receive a cardiac output recorded by the means 300 for recording a cardiac output.

The means 300 for recording cardiac output and stroke volume may be as follows:
1) Non-invasive, like:
   Doppler echocardiography
   Bioimpedance
   Bioreactance
   Diastolic pulse wave analysis or other current pulse contour methods
   MRI
   Scintigraphy
2) Invasive, like:
   Thermodilution
3) means implementing empirical equations; Indeed, stroke volume and thus cardiac output may be estimated on the basis of previous empirical regression lines obtained according to age, gender, body height, body weight, and level of fitness. It is likely that such a method will be the preferred way to estimate SV in large population, and in patients with hypertension, heart diseases, diabetes and lipid abnormalities.

During step 40, the indice of arterial stiffness is calculated:
according to equation 5, if the calculated indice of arterial stiffness is the characteristic impedance Zc:

$$Zc = [(Pi-DAP)*ST]/(2SV)$$

Zc being thus calculated as a function of DAP the diastolic pressure, Pi the pressure at the inflection point during systole, SV the recorded stroke volume of the artery, and ST the systolic time; more precisely, the characteristic impedance Zc is calculated as a function of the ratio $$[Pi-DAP]/SV \left( \text{that can also be written } \frac{(Pi-DAP)}{SV} \right)$$

according to equation 8, if the calculated indice of arterial stiffness is the waveguide function Zc/Rs:

$$Zc/Rs = [(Pi-DAP)/(MAP-Po)]*[(ST)/(2T)]$$

Zc/Rs being thus calculated as a function of DAP the diastolic pressure, Pi the pressure at the inflection point during systole, ST the systolic time, T the period, MAP the mean aortic pressure and Po the mean downstream pressure; more precisely, the waveguide function Zc/Rs is calculated as a function of the ratio $$ST/T \left(\text{that can also be written } \frac{ST}{T}\right) \text{ and as a function of the ratio} (Pi-DAP)/(MAP-Po) \left(\text{that can also be written } \frac{(Pi-DAP)}{(MAP-Po)}\right)$$

according to equation 13, if the calculated indice of arterial stiffness is the total arterial compliance C:

$$C=(SV*\Delta t)/[(Pi-DAP)*ST]$$

C being thus calculated as a function of DAP the diastolic pressure, Pi the pressure at the inflection point during systole, SV the recorded stroke volume of the artery, ST the systolic time, and $\Delta t$ the time to the pressure at the inflection point during systole; more precisely, the total arterial compliance C is calculated as a function of the ratio $$ST/\Delta t \left(\text{that can also be written } \frac{ST}{\Delta t}\right) \text{ and as a function of the ratio } [Pi-DAP]/SV \left(\text{that can also be written } \frac{(Pi-DAP)}{SV}\right)$$

according to equation 14, if the calculated indice of arterial stiffness is the total arterial stiffness 1/C:

$$1/C=[(Pi-DAP)*ST]/(SV*\Delta t)$$

1/C being thus calculated as a function of DAP the diastolic pressure, Pi the pressure at the inflection point during systole, SV the recorded stroke volume of the artery, ST the systolic time, and $\Delta t$ the time to the pressure at the inflection point during systole; more precisely, the total arterial stiffness 1/C is calculated as a function of the ratio $$ST/\Delta t \left(\text{that can also be written } \frac{ST}{\Delta t}\right) \text{ and as a function of the ratio } [Pi-DAP]/SV \left(\text{that can also be written } \frac{(Pi-DAP)}{SV}\right).$$

The characteristic impedance Zc, the total arterial compliance C and the total arterial stiffness 1/C are calculated as a function of the following ratio:

$$[(Pi-DAP)*ST]/SV \left(\text{that can also be written } \frac{(Pi-DAP)ST}{SV}\right)$$

The total arterial compliance C and the total arterial stiffness 1/C are calculated as a function of the following ratio:

$$[(Pi-DAP)*ST]/(SV*\Delta t) \left(\text{that can also be written } \frac{(Pi-DAP)ST}{SV\Delta t}\right)$$

During step 40, more than one indice of arterial stiffness can be calculated among the characteristic impedance Zc, the total arterial compliance C, the total arterial stiffness 1/C, and the waveguide function Zc/Rs.

Limitations

The new formulae are preferably applicable for invasive methods, and this impacts on their clinical application. The precise calculation of time and pressure variables, especially aortic Pi, is a prerequisite to our formulae. The systolic aortic pressure and PP reconstructed from radial artery applanation tonometry have been satisfactorily validated against pressure simultaneously recorded by micromanometers [11, 28], but the high-frequency components of the pulse-wave, including Pi and thus time to-Pi ($\Delta t$), appear less reliable [29]. Thus, the validation or the use of our formulae may be ideally used with invasive, high fidelity pressure recordings rather than with radial applanation tonometric devices.

The shape of the aortic flow wave may deviate from the triangular hypothesis in clinical situations such a low flow states and heart failure. The formulae proposed here strictly apply to steady state conditions in resting humans, but could also apply to non resting patients, especially during daily activity.

Potential Implications

The new formulae proposed here may furnish valuable and rapid estimates of pulsatile load in various populations, both at baseline and after therapeutic interventions. The formulae clearly illustrate the fact that time indices (systolic time ST, heart period T, and time-to-the first reflection wave $\Delta t$) and the indices quantifying arterial stiffness and pulsatile load are intrinsically related.

Numerous studies performed during the past three decades have documented that the resting heart rate is an independent cardiovascular risk factor in patients with cardiovascular diseases, heart failure, diabetes mellitus, and hypertension [30]. The resting heart rate (HR, in beats/min) is related to the resting heart period T (in seconds) according to the following formula:

$$HR=60/T \qquad (\text{equation 15})$$

The positive association frequently observed between increased heart rate and increased systolic and pulse pressure has been mainly attributed to an increased sympathetic drive. It is intuitive that both an increased pulsatile pressure and a high heart rate may be especially deleterious and contribute to both the increased pulsatile stretch put on the large arteries and the increased load put on the left ventricle. However, to the best of our knowledge, yet there has been no useful analytical formula relating pulsatile load and time intervals. One implication of our study is that only the waveguide ratio (equation 8) is mathematically related to heart rate. Conversely, equations 5, 13, and 14 indicate that Zc, C, and 1/C are mathematically dependent upon ST, not heart rate. The heart rate-independence of the mathematical formalisms of Zc, C, and 1/C we documented here is consistent with basic hemodynamical grounds [10].

Finally, the new indices we propose here may be also valuable in the specific area of the intensive care unit, where rapid changes in cardiac output must be monitored [31]. In the critically ill patient and following an initial calibration set with calculation of the reference, calibrated value of C ($C_{cal}$), systolic pulse contour analysis may help predict stoke volume changes assuming an essentially unchanged $C_{cal}$ after dynamic events [14]. Rearranging equation 13 led to the following equation:

$$SV=C_{cal}*[(Pi-DAP)*ST/\Delta t] \qquad (\text{equation 16})$$

Provided that a reliable estimation of aortic pressure, and especially Pi, is available, the formula may help track SV changes after fluid infusion, vasoactive drugs, and hemofiltration. The formula may not apply in cases where pressure-dependent changes in C are observed (eg, after severe hemorrhage).

The operating procedure also includes the monitoring of rapid changes in cardiac output by rearranging formula (5). Following an initial calibration set with calculation of the reference, calibrated value of Zc ($Zc_{cal}$), systolic pulse contour analysis may help predict stoke volume changes assuming an essentially unchanged $Zc_{cal}$ after dynamic events. Rearranging equation #5 led to the following equation:

$$SV=[(Pi-DAP) \times ST/2Zc_{cal}] \quad \text{(equation 17)}$$

The formula (17) may help tracking SV changes following fluid infusion, vasoactive drugs and hemofiltration. The formula (17) may be fruitfully compared to results from formula (16), and SV values obtained by the two formulas may also be averaged out to obtain a reliable estimate of SV.

Thus, after the steps 10, 20, 30, and 40 previously described, the first embodiment of a process according to the invention further comprises the subsequent step 50 of calibrating an indice of arterial stiffness. This indice is calibrated by calibration means 500. The calibrated indice of arterial stiffness is:
- a calibrated characteristic impedance $Zc_{cal}$, or
- a calibrated total arterial compliance $C_{cal}$, or
- a calibrated total arterial stiffness $1/C_{cal}$, the calibrated total arterial compliance $C_{cal}$ being equal to the inverse of the calibrated total arterial stiffness $1/C_{cal}$ The calibration of the indice 50 is set with the calculation of the indice calculated in step 40, that is:

$C_{cal}$ is set to the value of C previously calculated during step 40:

$$C_{cal}=C$$

and/or $1/C_{cal}$ is set to the value of $1/C$ previously calculated during step 40:

$$1/C_{cal}=1/C$$

and/or $Zc_{cal}$ is set to the value of Zc previously calculated during step 40:

$$Zc_{cal}=Zc$$

Furthermore more, the first embodiment of a process according to the invention according to the invention further comprises at least one new group of steps 10, 20 comprising:
- a new step 10 of recording the artery pressure, the newly recorded pressure being recorded as a function of time as illustrated in FIG. 1, the newly recorded pressure being recorded as a function of time by the means 100 for recording an artery pressure and time intervals; this new recording step 10 is similar to the recording step 10 previously described; and
- a new subsequent step 20 of extracting pulse wave analysis data from the newly recorded pressure during this new recording step 10, the newly extracted data being extracted by the means 200 for extracting pulse wave analysis data; this new extracting step 20 is similar to the extracting step 20 previously described.

After each iteration of a new group of steps 10, 20, the first embodiment of a process according to the invention further comprises the step 60 of calculating the stroke volume SV of the artery as a function of the calibrated indice and as a function of the data extracted in the new step 20 of this group of steps 10, 20. The stroke volume SV is calculated by means 600 for calculating SV.

The new groups of steps 10, 20 are preferably periodically and/or almost continuously iterated, for monitoring and tracking changes of the stroke volume SV. Thus, this embodiment of device and process according to the invention is preferably used in medical and surgical Intensive Care Unit (ICU) and in anesthesia unit, wherein such monitoring can be very useful.

The means 600 of calculating SV may be as follows:
standard calculations according to equations 16 and 17.
for SV calculation, averaging equations 16 and 17 results may be also used.

The means 600 of calculating can comprise a computer, a microprocessor, a digital circuit or an analogical circuit. The means 600 of calculating can comprise an input arranged to receive the analysis data extracted by the extracting means 200 and to receive a cardiac output recorded by the means 300 for recording a cardiac output.

The means 100, 200, 300, 400, 600 previously described can be connected together and arranged for automatically monitoring in time Zc, C, 1/C, waveguide ratio and/or SV.

The same means 400, 600 are used for calculating Zc, C, 1/C, waveguide ratio and SV. In the embodiment illustrated in FIG. 4, the extracting means 200, calculating means 400, 600 and calibrating means 500 are one computer.

During each new iteration of a new group of steps 10, 20, the newly extracted pulse wave analysis data comprise:
- a new value of the diastolic pressure DAP,
- a new value of the pressure Pi at the inflection point during systole,
- a new value of the systolic time ST, the stroke volume SV being calculated as a function of DAP, Pi, ST, and more precisely as a function of:

$(Pi-DAP)*ST$ (that can also be written: $(Pi-DAP)ST$)

The stroke volume SV can further be calculated as a function of Lt.

If, during the calibration step 50, the calibrated indice of arterial stiffness is the calibrated characteristic impedance $Zc_{cal}$, the stroke volume SV is calculated according to the following equation:

$$SV = [(Pi - DAP)*ST / (2Zc_{cal})]$$

$$SV = \frac{(Pi - DAP)ST}{2Z_{cal}},$$

where $Zc_{cal}$ is the calibrated characteristic impedance, DAP is the new value of the diastolic pressure, Pi is the new value of the pressure at the inflection point during systole, SV is the calculated stroke volume, and ST is the new value of the systolic time.

If, during the calibration step 50, the calibrated indice of arterial stiffness is the calibrated total arterial compliance $C_{cal}$ or the calibrated total arterial stiffness $1/C_{cal}$, then the newly extracted data further comprise a new value of the time $\Delta t$ to the pressure at the inflection point during systole, the stroke volume being calculated according to the following equation:

$$SV = C_{cal} * \left[ \frac{(Pi - DAP)*}{ST/\Delta t} \right] = 1/(1/C_{cal})*[(Pi - DAP)*ST/\Delta t]$$

$$SV = C_{cal}(Pi - DAP)\frac{ST}{\Delta t} = \frac{1}{1/C_{cal}}(Pi - DAP)\frac{ST}{\Delta t},$$

where DAP is the new value of the diastolic pressure, Pi is the new value of the pressure at the inflection point during systole, SV is the calculated stroke volume, ST is the new value of the systolic time, and Δt is the new value of the time to the pressure at the inflection point during systole.

If, during the calibration step 50, more than one indice of arterial stiffness are calibrated, the calibrated indices of arterial stiffness comprising:
- the calibrated characteristic impedance $Zc_{cal}$, and
- the calibrated total arterial compliance $C_{cal}$ or the calibrated total arterial stiffness $1/C_{cal}$, then the stroke volume is calculated by averaging equations 16 and 17, i.e. the stroke volume is calculated by averaging:
- a calculation of the stroke volume as a function of the calibrated characteristic impedance $Zc_{cal}$, and
- a calculation of the stroke volume as a function of the calibrated total arterial compliance $C_{cal}$ or the calibrated total arterial stiffness $1/C_{cal}$, for example by doing the following calculations:

$$SV1 = C_{cal} * [(Pi-DAP)*ST/\Delta t]$$

$$SV2 = [(Pi-DAP)*ST/(2Zc_{cal})]$$

$$SV = f(SV1, SV2)$$

Where f is a function of SV1 and SV2, f being for example equal to:

$$SV = f(SV1, SV2) = [SV1+SV2]/2$$

Figure 5:
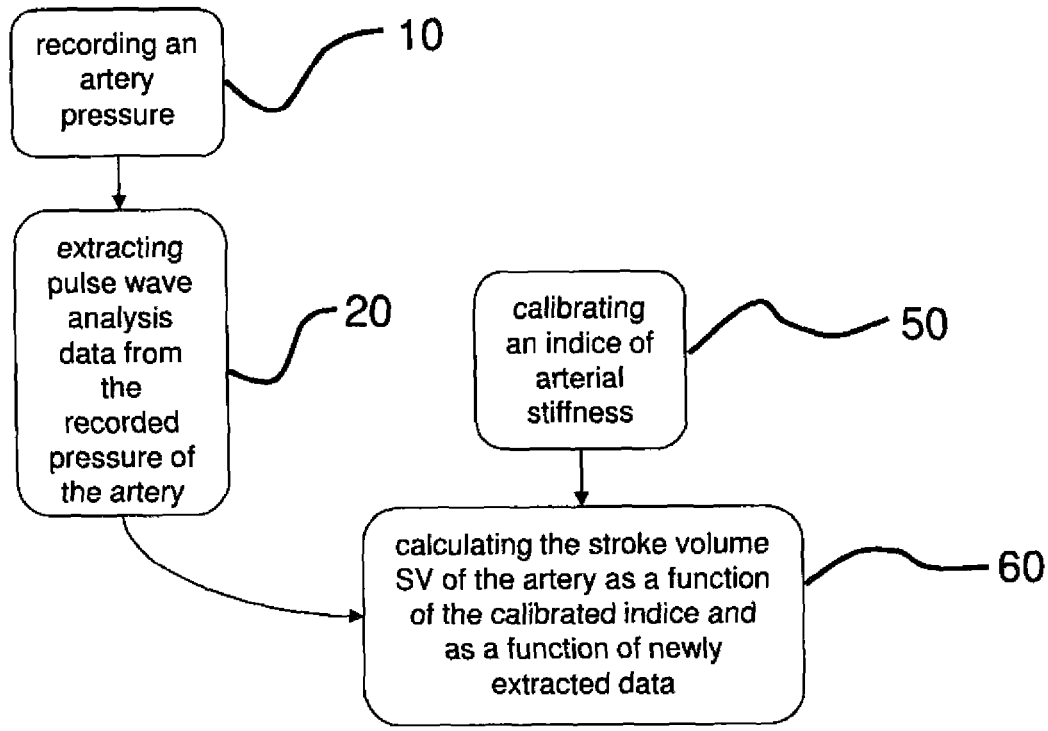
FIG. 5 is a schematic representation of a second embodiment of a process according to the invention.

In references to FIGS. 1, 5 and 6, a second embodiment of the process according to the invention will now be described only for its differences compared to the first embodiment previously described. In particular, references 1 to 7, 10, 20, 50, 60, 100, 200, 500 and 600 will not be described once again.

Figure 6:
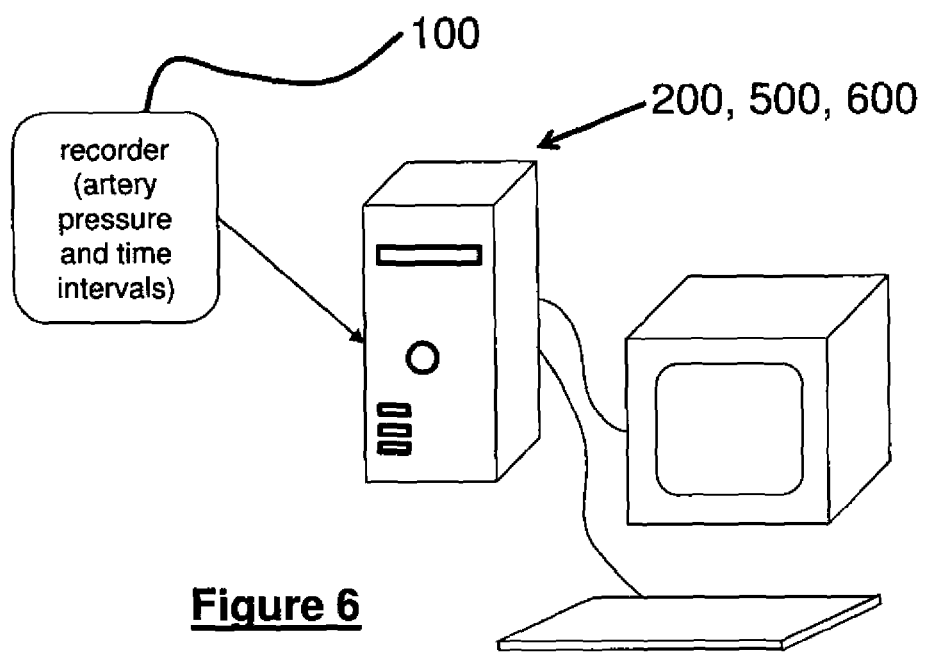
FIG. 6 is a schematic representation of a device according to the invention implementing the second embodiment of a process according to the invention.

This second embodiment of the process according to the invention is implemented by the device according to the invention illustrated in FIG. 6.

This second embodiment of the process according to the invention comprises:
- the previously described at least one (preferably many) group(s) of recording 10 and extracting 20 steps implemented respectively by the previously described means 100 and 200,
- a step 50 of calibrating an indice of arterial stiffness, implemented by the previously described means 500,
- the previously described step 60 of calculating the stroke volume SV, implemented by the previously described means 600 for each group of steps 10, 20.

The differences compared to the first embodiment of the process according to the invention are:
- the second embodiment of the process according to the invention does not comprise the previously described steps 30 and 40, and
- in the second embodiment of the process according to the invention, during the calibrating step 50, the calibrated indice of arterial stiffness $Zc_{cal}$, $C_{cal}$ or $1/C_{cal}$ is fixed arbitrarily according to age, gender, body height, body weight, and/or level of fitness of the person whose artery is studied.

Thus, the second embodiment of the process according to the invention does not require any previous calculation of Zc, C or 1/C, but still allows monitoring and tracking changes of SV. This embodiment of device and process according to invention is preferably used in medical and surgical Intensive Care Unit (ICU) and in anesthesia unit, wherein such monitoring can be very useful.

CONCLUSION

Here we have proposed four new hemodynamical formulae (equations 5, 8, 13, and 14) derived from systolic pulse contour analysis and relating the characteristic impedance (Zc), the waveguide ratio (Zc/Rs), total arterial compliance (C), and total arterial stiffness (1/C) to simple aortic pressure indices and time indices. The mathematical relationship between pulsatile load indices and time intervals was stressed, with Zc being mathematically related to ST, the waveguide ratio being related to the duty cycle (ST/T), and 1/C being related to the ST/Δt ratio.

Unlike previous studies performed on the basis of diastolic pulse contour analysis, our systolic pulse contour analysis relies on the propagative model, not the windkessel model, and thus avoids the theoretical limitations related to the latter model. Our proposal incorporates the potential influences of wave propagation and reflections on the indices of pulsatile load. The present viewpoint is mainly based on 2 validated hypotheses: (1) a linear aortic pressure-flow relationship in early systole, (ie, before the arrival of the first reflected wave) and (2) a triangular aortic flow wave during systole. While the former hypothesis intrinsically belongs to the characteristic impedance concept, the latter may be inaccurate in low flow states or in arrhythmic patients. The main limitation of our study is that the new formulae are mainly applicable for invasive methods, and this affects on their clinical application. However, in the near future, it may be expected that improved tonometric devices may well furnish more reliable estimates of the high-frequency components of the pulse wave, allowing a more reliable, noninvasive estimation of pulsatile load.

Of course, the invention is not limited to the examples which have just been described and numerous amendments can be made to these examples without exceeding the scope of the invention.

In particular, the previously described embodiments mainly concern an heart artery, but the invention may be applied to any other artery, in the human or other animals. For example, the operating procedure may also involve pulmonary artery pulse wave analysis, by using the procedures described above. This may allow to estimate pulmonary artery characteristic impedance Zc, waveguide ration Zc/Rs, compliance C and stiffness 1/C according to similar formulae 5, 8, 13, and 14 and to track right ventricular stroke volume changes according to equations 16 and 17.

Furthermore, the calculations of the process according to the invention may be obtained under various clinical settings: health and diseases, throughout aging, at rest and exercise, during day and night, before and after dynamic maneuvers, before and after acute or chronic therapy.

CITED REFERENCES

[1]. Nichols W W. Clinical measurements of arterial stiffness obtained from noninvasive pressure waveforms. Am J. Hypertens. 2005; 18:3S-10S.

[2]. O'Rourke M F. Mechanical factors in arterial aging. A clinical perspective. J Am Coll Cardiol. 2007; 50:1-13.

[3]. Mitchell G F. Arterial stiffness and wave reflection in hypertension: pathophysiologic and therapeutic implications. Curr Hypertens Reports. 2004; 6:436-441.

[4]. Safar M E, Levy B I. Current perspectives on arterial stiffness and pulse pressure in hypertension and cardiovascular disease. Circulation. 2003; 107:2864-2869.

[5]. Oliver J J, Webb D J. Noninvasive assessment of arterial stiffness and risk of atherosclerotic events. Arterioscler Thromb Vasc Biol. 2003; 23:554-566.

[6]. Laurent S, Cockcroft J, van Bortel L, et al. Expert consensus document on arterial stiffness: methodological and clinical applications. Eur Heart J. 2006; 27:2588-2605.

[7]. Murgo J P, Westerhof N, Giolma J P, et al. Aortic input impedance in normal man: relationship to pressure wave forms. Circulation. 1980; 62:105-116.

[8]. van den Bos G C, Westerhof N, Randall O S. Pulse wave reflection: can it explain the differences between systemic and pulmonary pressure and flow waves? Circ Res. 1982; 51:479-485.

[9]. Skalak R. Synthesis of a complete circulation. In: Cardiovascular Fluid Dynamics. Bergel D H, ed. New York: Academic Press; 1972:341-376.

[10]. Milnor W R. Hemodynamics. Baltimore: Williams & Wilkins; 1982.

[11]. Nichols W W, O'Rourke M F. McDonalds blood flow in arteries: theoretical, experimental and clinical principles. 5th edition. Edwards A, ed. London: Oxford University Press; 2005.

[12]. Quick C M, Berger D S, Stewart R H, et al. Resolving the hemodynamic inverse problem. IEEE Trans Biomed Eng. 2006; 53:361-368.

[13]. Sagawa K, Lie R K, Schaefer J. Translation of Otto Frank's paper "Die Grundform des Arteriellen Pulses" Zeitschrift fuür Biologie 37: 483-526 (1899) J Mol Cell Cardiol. 1990; 22:253-277.

[14]. Bourgeois M J, Gilbert B K, Donald D E, et al. Characteristics of aortic diastolic pressure decay with application to the continuous monitoring of changes in peripheral vascular resistance. Circ Res. 1974; 35:56-66.

[15]. Liu Z, Brin K, Yin F. Estimation of total arterial compliance: an improved method and evaluation of current methods. Am J. Physiol. 1986; 251: H588-H600.

[16]. Chemla D, Hébert J L, Coirault C, et al. Total arterial compliance estimated by the stroke volume-to-aortic pulse pressure ratio in humans. Am J. Physiol. 1998; 274:H500-H505.

[17]. Stegiopulos N, Segers P, Westerhof N. Use of pulse pressure method for estimating total arterial compliance in vivo. Am J. Physiol. 1999; 276: H424-H428.

[18]. Mitchell G F, Pfeffer M A. Evaluation and management of patients with uncontrolled systolic hypertension: Is another new paradigm needed? Am Heart J. 2005; 149: 176-184.

[19]. Dujardin J P L, Stone D N. Characteristic impedance of the proximal aorta determined for the time domain and frequency domain. A comparison. Med Biol Eng Comput. 1981; 19:565-568.

[20]. Lucas C L, Wilcox B R, Ha B, et al. Comparison of time domain algorithms for estimating aortic characteristic impedance in humans. IEEE Trans Biomed Eng. 1988; 35:62-68.

[21]. Mitchell G F, Lacourcière Y, Arnold M O, et al. Changes in aortic stiffness and augmentation index after acute converting enzyme or vasopeptidase inhibition. Hypertension. 2005; 46:1111-1117.

[22]. Mitchell G F, Arnold W O, Dunlap M E, et al. Pulsatile hemodynamic effects of candesartan in patients with chronic heart failure: the CHARM program. Eur J Heart Fail. 2006; 8:191-197.

[23]. Kelly R, Hayward C, Avolio A, et al. Noninvasive determination of age-related changes in the human pulse. Circulation. 1989; 80:1652-1659.

[24]. Westerhof B E, Guelen I, Westerhof N, et al. Quantification of wave reflection in the human aorta from pressure alone. A proof of principle. Hypertension. 2006; 48:595-601.

[25]. Williams B, Lacy P S, Thom S M, et al. Differential impact of blood pressure-lowering drugs on central aortic pressure and clinical outcomes. Principal results of the conduit artery function evaluation (CAFE) study. Circulation. 2006; 113:1213-1225.

[26]. Weber T, Auer J, O'Rourke M F, et al. Prolonged mechanical systole and increased arterial wave reflections in diastolic dysfunction. Heart. 2006; 92:1616-1622.

[27]. Lau E O Y, Tse H F, Chan R H W, et al. Prediction of aortic augmentation index using radial pulse transmission-wave analysis. J. Hypertens. 2006; 24:723-730.

[28]. Agabiti-Rosei E, Mancia G, O'Rourke M F, et al. Central blood pressure measurements and antihypertensive therapy. A consensus document. Hypertension. 2007; 50:154-160.

[29]. Hope S A, Tay D B, Meredith I B, et al. Comparison of generalized and gender-specific transfer functions for the derivation of aortic waveforms. Am J. Physiol. 2002; 283: H1150-H1156.

[30]. Palatini P, Benetos A, Julius S. Impact of increased heart rate on clinical outcomes in hypertension: implications for drug therapy. Drugs. 2006; 66: 133-144.

[31]. Michard F, Boussat, Chemla D, et al. Relation between respiratory changes in arterial pulse pressure and fluid responsiveness in septic patients with acute circulatory failure. Am J Resp Crit Care Med. 2000; 162:134-138.

The invention claimed is:

1. A process for calculating an indice of arterial stiffness of a human or another animal, comprising:
    recording an artery pressure as a function of time from the human or another animal;
    providing a processor configured to perform the following steps:
    extracting pulse wave analysis data from the recorded pressure of the artery of the human or another animal,
    calculating the indice of arterial stiffness of the human or another animal as a function of the extracted pulse wave analysis data comprising:
    at least one extracted time interval including an extracted systolic time, and
    an extracted diastolic pressure and an extracted pressure at an inflection point during systole, wherein the inflection point is not an inflexion point at the beginning of systole or at the end of systole,
    the indice of arterial stiffness of the human or another animal being thus calculated as a function of the extracted systolic time, the extracted diastolic pressure and the extracted pressure at said inflection point during systole; and
    monitoring, in time, the calculated indice of arterial stiffness of the human or another animal in one of a medical unit, a surgical intensive care unit or an anesthesia unit.

2. The process according to claim 1, wherein the at least one time interval comprises a time to the pressure at an inflection point during systole, the indice being calculated as a function of the ratio: $ST/\Delta t$, where $\Delta t$ is the time to the pressure at the inflection point during systole and ST is the systolic time.

3. The process according to claim 1, wherein the at least one time interval comprises a period of the artery, the indice being calculated as a function of the ratio: $ST/T$, where T is the period and ST is the systolic time.

4. The process according to claim 1, wherein the indice of arterial stiffness is a characteristic impedance calculated according to the following equation:

$$Zc=[(Pi-DAP)*ST]/(2SV),$$

where Zc is the characteristic impedance, DAP is the diastolic pressure, Pi is the pressure at the inflection point during systole, SV is a recorded stroke volume, and ST is the systolic time.

5. The process according to claim 2, wherein the indice of arterial stiffness is a total arterial compliance calculated according to the following equation:

$$C=(SV*\Delta t)/[(Pi-DAP)*ST],$$

where C is the total arterial compliance, DAP is the diastolic pressure, Pi is the pressure at the inflection point during systole, SV is a recorded stroke volume, ST is the systolic time, and $\Delta t$ is the time to the pressure at the inflection point during systole.

6. The process according to claim 2, wherein the indice of arterial stiffness is a total arterial stiffness calculated according to the following equation:

$$1/C=[(Pi-DAP)*ST]/(SV*\Delta t),$$

where 1/C is the total arterial stiffness, DAP is the diastolic pressure, Pi is the pressure at the inflection point during systole, SV is a recorded stroke volume, ST is the systolic time, and $\Delta t$ is the time to the pressure at the inflection point during systole.

7. The process according to claim 3, wherein the indice of arterial stiffness is a waveguide function, the extracted pulse wave analysis data comprising:
a mean aortic pressure,
a mean downstream pressure
the waveguide function being calculated according to the following equation:

$$Zc/Rs=[(Pi-DAP)/(MAP-Po)]*[(ST)/(2T)],$$

where Zc/Rs is the waveguide function, DAP is the diastolic pressure, Pi is the pressure at the inflection point during systole, ST is the systolic time, T is the period, MAP is the mean aortic pressure and Po is the mean downstream pressure.

8. The process according to claim 1, comprising:
setting a calibrated indice of arterial stiffness equal to the previously calculated indice of arterial stiffness;
calculating a stroke volume as a function of the calibrated indice and as a function of:

$$(Pi-DAP)*ST$$

where DAP is the diastolic pressure, Pi is the pressure at the inflection point during systole, and ST is the systolic time.

9. The process according to claim 8, wherein the indice of arterial stiffness is a characteristic impedance, the calculated stroke volume being calculated according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time.

10. The process according to claim 8, wherein the indice of arterial stiffness is a total arterial compliance or a total arterial stiffness, the at least one time interval further comprising a time to the pressure at the inflection point during systole, the calculated stroke volume being calculated according to the following equation:

$$SV=C_{cal}*[(Pi-DAP)*ST/\Delta t],$$

where $C_{cal}$ is the calibrated total arterial compliance that is equal to the inverse of the calibrated total arterial stiffness $1/C_{cal}$, DAP is the diastolic pressure, Pi is the pressure at the inflection point during systole, SV is the calculated stroke volume, ST is the systolic time, and $\Delta t$ is the time to the pressure at the inflection point during systole.

11. A process for calculating a stroke volume of a human or another animal, comprising:
recording an artery pressure as a function of time from the human or another animal;
providing a processor configured to perform the steps of:
extracting pulse wave analysis data from the recorded pressure of an artery of the human or another animal;
calculating the stroke volume of the human or another animal as a function of the extracted pulse wave analysis data including:
at least one extracted time interval including an extracted systolic time, and
an extracted diastolic pressure and an extracted pressure at an inflection point during systole, wherein the inflection point is not an inflexion point at the beginning of systole or at the end of systole,
the stroke volume of the human or another animal being thus calculated as a function of the extracted systolic time, the extracted diastolic pressure and the extracted pressure at said inflection point during systole; and
monitoring, in time, the calculated stroke volume of the human or another animal in one of a medical unit, a surgical intensive care unit or an anesthesia unit.

12. The process according to claim 11, wherein the calculated stroke volume is calculated as a function of:

$$(Pi-DAP)*ST,$$

where DAP is the diastolic pressure, Pi is the pressure at the inflection point during systole, and ST is the systolic time.

13. The process according to claim 11, wherein the calculated stroke volume is calculated according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time.

14. The process according to claim 11, wherein the at least one time interval further comprises a time to the pressure at the inflection point during systole, the calculated stroke volume being calculated according to the following equation:

$$SV=C_{cal}*[(Pi-DAP)*ST/\Delta t],$$

where $C_{cal}$ is a calibrated total arterial compliance that is equal to the inverse of a calibrated total arterial stiffness $1/C_{cal}$, DAP is the diastolic pressure, Pi is the pressure at the inflection point during systole, SV is the calculated stroke volume, ST is the systolic time, and $\Delta t$ is the time to the pressure at the inflection point during systole.

15. A device for calculating an indice of arterial stiffness of a human or another animal, comprising:
a processor including:
means for recording an artery pressure as a function of time from the human or another animal;
means for extracting pulse wave analysis data from the recorded pressure of the artery of the human or another animal, the recorded pressure being recorded as a function of time; and
means for calculating the indice of arterial stiffness of the human or another animal as a function of the extracted pulse wave analysis data comprising:

at least one extracted time interval including an extracted systolic time, and an extracted diastolic pressure and an extracted pressure at an inflection point during systole, wherein the inflection point is not an inflexion point at the beginning of systole or at the end of systole, the indice of arterial stiffness of the human or another animal being thus calculated as a function of the extracted systolic time, the extracted diastolic pressure and the extracted pressure at said inflection point during systole; and means for monitoring, in time, the calculated indice of arterial stiffness of the human or another anima one of a medical unit, a surgical intensive care unit or an anesthesia unit.

16. The device according to claim 15, wherein the at least one time interval comprises a time to the pressure at an inflection point during systole, the means for calculating the indice of arterial stiffness being arranged for calculating the indice as a function of the ratio:

$ST/\Delta t$, where $\Delta t$ is the time to the pressure at the inflection point during systole and ST is the systolic time.

17. The device according to claim 15, wherein the at least one time interval comprises a period of the artery, the means for calculating the indice of arterial stiffness being arranged for calculating the indice as a function of the ratio:

$ST/T$, where T is the period and ST is the systolic time.

18. The device according to claim 15, further comprising means for recording a stroke volume, the means for calculating the indice of arterial stiffness being arranged for calculating the indice as a function of the recorded stroke volume.

19. The device according to claim 15, wherein the indice of arterial stiffness is a characteristic impedance, the means for calculating the indice of arterial stiffness being arranged for calculating the characteristic impedance according to the following equation:

$$Zc=[(Pi-DAP)*ST]/(2SV),$$

where Zc is the characteristic impedance, DAP is the diastolic pressure, Pi is the pressure at the inflection point during systole, SV is a recorded stroke volume, and ST is the systolic time.

20. The device according to claim 16, wherein the indice of arterial stiffness is a total arterial compliance, the means for calculating the indice of arterial stiffness being arranged for calculating the total arterial compliance according to the following equation:

$$C=(SV*\Delta t)/[(Pi-DAP)*ST],$$

where C is the total arterial compliance, DAP is the diastolic pressure, Pi is the pressure at the inflection point during systole, SV is a recorded stroke volume, ST is the systolic time, and $\Delta t$ is the time to the pressure at the inflection point during systole.

21. The device according to claim 16, wherein the indice of arterial stiffness is a total arterial stiffness, the means for calculating the indice of arterial stiffness being arranged for calculating the total arterial stiffness according to the following equation:

$$1/C=[(Pi-DAP)*ST]/(SV*\Delta t),$$

where 1/C is the total arterial stiffness, DAP is the diastolic pressure, Pi is the pressure at the inflection point during systole, SV is a recorded stroke volume, ST is the systolic time, and $\Delta t$ is the time to the pressure at the inflection point during systole.

22. The device according to claim 17, wherein the indice of arterial stiffness is a waveguide function, the extracted pulse wave analysis data comprising:

a mean aortic pressure, a mean downstream pressure, the means for calculating the indice of arterial stiffness being arranged for calculating the waveguide function according to the following equation:

$$Zc/Rs=[(Pi-DAP)/(MAP-Po)]*[(ST)/(2T)],$$

where Zc/Rs is the waveguide function, DAP is the diastolic pressure, Pi is the pressure at the inflection point during systole, ST is the systolic time, T is the period, MAP is the mean aortic pressure and Po is the mean downstream pressure.

23. The device according to claim 22, comprising a calibration means configured for setting a calibrated indice of arterial stiffness equal to an indice of arterial stiffness previously calculated by the means for calculating the indice of arterial stiffness, the device further comprising means for calculating a stroke volume as a function of the calibrated indice and as a function of:

$$(Pi-DAP)*ST$$

where DAP is the diastolic pressure, Pi is the pressure at the inflection point during systole, and ST is the systolic time.

24. The device according to claim 23, wherein the means for calculating a stroke volume is configured to monitor and track changes.

25. The device according to claim 23, wherein the indice of arterial stiffness is a characteristic impedance, the means for calculating a stroke volume being arranged for calculating the stroke volume according to the following equation:

$$SV=[(Pi-DAP)*ST/(2Zc_{cal})],$$

where $Zc_{cal}$ is the calibrated characteristic impedance, DAP is the diastolic pressure, Pi is the pressure at the inflection point during systole, SV is the calculated stroke volume, and ST is the systolic time.

26. The device according to claim 23, wherein the indice of arterial stiffness is a total arterial compliance or a total arterial stiffness, the at least one time interval further comprising a time to the pressure at the inflection point during systole, the means for calculating a stroke volume being arranged for calculating the stroke volume according to the following equation:

$$SV=C_{cal}*[(Pi-DAP)*ST/\Delta t],$$

where $C_{cal}$ is the calibrated total arterial compliance that is equal to the inverse of the calibrated total arterial stiffness $1/C_{cal}$, DAP is the diastolic pressure, Pi is the pressure at the inflection point during systole, SV is the calculated stroke volume, ST is the systolic time, and $\Delta t$ is the time to the pressure at the inflection point during systole.

27. A device for calculating a stroke volume of a human or another animal, comprising:

means for recording an artery pressure as a function of time from the human or another animal;

a processor including:

means for extracting pulse wave analysis data from a recorded pressure of an artery of the human or another animal, the recorded pressure being recorded as a function of time; and means for calculating the stroke volume of the human or another animal as a function of the extracted data, wherein the extracted pulse wave analysis data comprises:
- at least one extracted time interval including an extracted systolic time, and
- an extracted diastolic pressure and an extracted pressure at an inflection point during systole, wherein the inflection point is not an inflexion point at the beginning of systole or at the end of systole,
- the stroke volume of the human or another animal being thus calculated as a function of the extracted systolic time, the extracted diastolic pressure and the extracted pressure at said inflection point during systole; and means for monitoring, in time, the calculated stroke volume of the human or another animal in one of a medical unit, a surgical intensive care unit or an anesthesia unit.

28. The device according to claim 27, wherein the means for calculating a stroke volume is arranged for calculating the stroke volume as a function of:

$$(Pi-DAP)*ST,$$

where DAP is the diastolic pressure, Pi is the pressure at the inflection point during systole, and ST is the systolic time.

29. The device according to claim 27, wherein the means for calculating a stroke volume are arranged for calculating the stroke volume according to the following equation:

$$SV=[(Pi-DAP)*ST/(2Zc_{cal})],$$

where $Zc_{cal}$ is a calibrated characteristic impedance, DAP is the diastolic pressure, Pi is the pressure at the inflection point during systole, SV is the calculated stroke volume, and ST is the systolic time.

30. The device according to claim 27, wherein the at least one time interval further comprises a time to the pressure at the inflection point during systole, the means for calculating a stroke volume being arranged for calculating the stroke volume according to the following equation:

$$SV=C_{cal}*[(Pi-DAP)*ST/\Delta t],$$

where $C_{cal}$ is a calibrated total arterial compliance that is equal to the inverse of a calibrated total arterial stiffness $1/C_{cal}$, DAP is the diastolic pressure, Pi is the pressure at the inflection point during systole, SV is the calculated stroke volume, ST is the systolic time, and $\Delta t$ is the time to the pressure at the inflection point during systole.

31. The process according to claim 1, wherein the indice is calculated as a function of:

$$(Pi-DAP)*ST$$

where DAP is the diastolic pressure, Pi is the pressure at the inflection point during systole, and ST is the systolic time.

32. The process according to claim 1, wherein the indice is calculated as a function of a recorded stroke volume.

33. The device according to claim 15, wherein the means for calculating the indice of arterial stiffness is arranged for calculating the indice as a function of:

$$(Pi-DAP)*ST$$

where DAP is the diastolic pressure, Pi is the pressure at the inflection point during systole, and ST is the systolic time.

34. The process of claim 1, wherein the processor includes one of: a computer or a microprocessor.

35. The process of claim 11, wherein the processor includes one of: a computer or a microprocessor.

36. The device of claim 15, wherein the processor includes one of: a computer or a microprocessor.

37. The device of claim 27, wherein the processor includes one of: a computer or a microprocessor.

* * * * *

UNITED STATES PATENT AND TRADEMARK OFFICE
CERTIFICATE OF CORRECTION

PATENT NO.         : 9,107,587 B2                    Page 1 of 1
APPLICATION NO.    : 12/866317
DATED              : August 18, 2015
INVENTOR(S)        : Chemla et al.

It is certified that error appears in the above-identified patent and that said Letters Patent is hereby corrected as shown below:

In the Claims:

| | |
|---|---|
| Col. 26, line 12, Claim 11 | Please delete "an" and insert --the-- therefor. |
| Col. 26, line 41, Claim 13 | Please delete "the" and insert --a-- therefor. |
| Col. 26, line 57, Claim 15 | After "comprising:", please insert the following new paragraph: |
| | --means for recording an artery pressure as a function of time from the human or another animal;--. |
| Col. 26, lines 59-60, Claim 15 | Please delete the following paragraph: |
| | "means for recording an artery pressure as a function of time from the human or another animal;". |
| Col. 28, line 64, Claim 27 | Please delete "a" and insert --the-- therefor. |
| Col. 28, line 65, Claim 27 | Please delete "an" and insert --the-- therefor. |

Signed and Sealed this
Fifteenth Day of March, 2016

Michelle K. Lee
*Director of the United States Patent and Trademark Office*